United States Patent [19]

Achener

[11] 4,222,414
[45] Sep. 16, 1980

[54] PULSE DAMPER FOR HIGH-PRESSURE LIQUID CHROMATOGRAPHY

[75] Inventor: Pierre Y. Achener, Walnut Creek, Calif.

[73] Assignee: Varian Associates, Inc., Palo Alto, Calif.

[21] Appl. No.: 48,320

[22] Filed: Jun. 14, 1979

Related U.S. Application Data

[63] Continuation of Ser. No. 881,285, Feb. 27, 1978, abandoned.

[51] Int. Cl.³ ............................................. F16L 55/04
[52] U.S. Cl. ...................................... 138/30; 210/198 C
[58] Field of Search .................... 138/30, 26; 417/540, 417/542; 239/89, 96; 210/198 C

[56] References Cited

U.S. PATENT DOCUMENTS

| | | | |
|---|---|---|---|
| 2,916,052 | 12/1959 | Peters | 138/30 |
| 3,605,815 | 9/1971 | Von Forell | 138/30 |
| 3,878,867 | 4/1975 | Dirks | 138/30 |
| 4,024,061 | 5/1977 | Gatiss | 417/540 |

Primary Examiner—Lenard A. Footland
Attorney, Agent, or Firm—Stanley Z. Cole; John J. Morrissey; Gerald M. Fisher

[57] ABSTRACT

A pulse damper for use in high-pressure liquid pumping applications, such as liquid chromatography, comprises a stainless steel cylindrical housing structure having threaded end caps to which inlet and outlet fittings are attached for coupling to a high-pressure liquid flow line. A spool made of a plastic material such as polytetrafluoroethylene or a perfluoroelastomer is fitted tightly within the housing structure, so that flow line liquid passes through the damper via the axial bore of the spool. The outer portion of the spool is configured to provide a cavity between the spool and the surrounding housing structure, and a compressible liquid fills this cavity. In operation, when a pressure pulse occurs in the flow line liquid, the relatively thin cylindrical wall of the spool expands radially outward in response, thereby causing a compression of the liquid in the surrounding cavity. Thus, the liquid in the cavity surrounding the spool serves as an energy-storing means for damping pulsations in the flow line.

2 Claims, 2 Drawing Figures

PULSE DAMPER FOR HIGH-PRESSURE LIQUID CHROMATOGRAPHY

This is a continuation of application Ser. No. 881,285, filed Feb. 27, 1978, now abandoned.

BACKGROUND OF THE INVENTION

This invention relates generally to liquid pumping systems in which the damping of pressure pulses in a high-pressure flow line is required.

A particular application of this invention is a high-pressure liquid chromatography system in which a carrier liquid containing a quantity of sample solution to be analyzed is sent to a chromatographic column in pulses by the action of a reciprocating pump. In order to provide a continuous flow of liquid to the chromatographic column, it is necessary to insert a pulse damper in the flow line between the pump and the chromatographic column.

In the prior liquid chromatography art, a block of plastic material such as polytetrafluoroethylene (available commercially under the Teflon trademark) was placed in the flow line between a reciprocating pump and a chromatographic column to serve as a pulse damper. Since a Teflon block is compressible, it can store energy by becoming compressed during that portion of the pumping cycle when the pressure in the flow line is rising, and can release the stored energy by decompressing when the pressure in the flow diminishes. Thus, over a complete pumping cycle, the pressure pulses generated in the flow line liquid by the reciprocating pump can be smoothed out before the flow line liquid reaches the chromatographic column. A pulse damper of this kind was described in U.S. Pat. No. 4,024,061.

With such prior art pulse damping devices in which a compressible body was disposed directly in the flow line, the choice of materials for the compressible body was generally limited to those plastics that are chemically inert with respect to the kinds of fluids used in liquid chromatography. Only a few plastic materials, such as polytetrafluoroethylene (Teflon) and polychlorotrifluoroethylene (Kel-F), can meet this requirement. Furthermore, the damping characteristics of a compressible plastic body are not adjustable. Thus, with the prior art pulse damping devices that utilized the compressibility of a plastic body as the pulse damping mechanism, it was not possible to match the damping characteristics of the pulse damper with the pulsing characteristics of the pump except by changing the volume of the compressible plastic material.

Also, with prior art pulse dampers having a compressible plastic body in a housing structure coupled to the flow line, unflushable "dead volumes" tended to occur in portions of the housing structures as the flow line fluid altered its course through the housing structure because of the obstacle provided by the compressible plastic body. Minute quantities of the flow line fluid tended to become trapped in such dead volumes, thereby becoming a source of contamination for the chromatographic system.

The compressibility of polytetrafluoroethylene at low pressures (i.e., in the range from atmospheric pressure to about 1000 psi) was well-known to the prior art. Apparently, the assumption also prevailed in the prior art that polytetrafluoroethylene would exhibit substantially similar compressibility characteristics at high pressures (i.e., above 1000 psi), as evidenced by the fact that pulse dampers utilizing the compressibility of a polytetrafluoroethylene body disposed directly in the flow line were used in the prior art even in high-pressure liquid chromatography applications. However, experimental work that resulted in the present invention has surprisingly revealed that the compressibility of polytetrafluoroethylene decreases quite rapidly with increasing pressure at pressures above 1000 psi. Consequently, the effectiveness of prior art pulse dampers at pressures above 1000 psi becomes severely reduced as flow line pressures increased.

SUMMARY OF THE INVENTION

It is an object of this invention to provide a novel pulse damper for use in liquid pumping systems, where the pulse damping mechanism utilizes the compressibility of a liquid.

It is likewise an object of this invention to provide a novel pulse damper for use in a liquid pumping system, where the damping characteristics of the pulse damper can be selected in accordance with the pulsing characteristics of the pump.

It is a particular object of this invention to provide a pulse damper for use in a liquid chromatography system in which a reciprocating pump delivers sample material dissolved in a carrier liquid to a chromatographic column for analysis; where the pulse damping mechanism does not require that a compressible body be inserted in the flow line between the pump and the chromatographic column.

It is an immediate object of this invention to provide a pulse damper for use in high-pressure liquid chromatography, which pulse damper provides a significant smoothing of the pulses delivered by a reciprocating pump at pressures above 1000 psi.

It is a feature of this invention that the pulse damping mechanism does not depend upon the compressibility of a plastic material.

It is likewise a feature of this invention that the pulse damping mechanism does not cause obstructions in the liquid flow line. In particular, the pulse damper does not comprise a solid object inserted in the flow line.

In a preferred embodiment of this invention, a compressible plastic body that is chemically compatible with the liquid being pumped is configured as a cylindrical spool having an axial bore therethrough. In liquid chromatographic applications, the spool is preferably made of polytetrafluoroethylene, which is chemically inert with respect to the solvents generally used. The spool is fitted tightly within a steel cylindrical housing structure, with threaded steel end caps serving to close the housing structure on either end. Suitable fittings are attached to the end caps to provide means for coupling inlet and outlet lines to respective ends of the housing structure, whereby the flow line fluid can pass through the axial bore of the spool. The outer surface of the spool is configured to form an annular cavity between the spool and the inner wall of the surrounding housing structure. Appropriate seals are located at both ends of the spool to isolate the flow line liquid from the cavity surrounding the spool. This cavity is filled with water or any other liquid that is compressible at high pressures.

In operation, when pressure pulses occur in the flow line liquid passing through the axial bore of the spool, the walls of the bore are deflected radially outward in response to such pulses. The liquid confined in the annular cavity around the spool is thereupon compressed. Thus, the liquid in the cavity serves as a medium for storing energy during the portion of the pumping cycle when the pulses occur. The relatively thin walls of the bore do not significantly compress in response to pulsations in the flow line liquid, but rather merely serve to transmit the force of these pulsations to the liquid confined in the cavity surrounding the spool. The liquid in the cavity, rather than the plastic spool, serves as the pulse-damping medium.

The pulse damping characteristics of a damper according to this invention can be varied by appropriate selection of the liquid used in the annular cavity. Since the liquid in the annular cavity is isolated from the liquid being pumped through the spool, the choice of liquid for use in the annular cavity does not depend upon the chemical composition of the liquid being pumped.

A significant feature of a pulse damper according to the present invention is that the flexible-walled bore of the spool expands radially outward in response to pulsations in the outflow from the reciprocating pump so that the energy of these pulsations is absorbed by the compressible liquid surrounding the spool, thereby damping pulsations in the line. Because there are no obstacles in the flow line, a pulse damper according to the invention avoids causing hydrodynamic disruptions in the flow through the flow line. In the preferred embodiment, the diameter and length of the axial bore through the plastic spool are selected so that the volume of liquid within the pulse damper is about the same as the volume of liquid delivered by the reciprocating pump during a single pulse.

DESCRIPTION OF THE PREFERRED EMBODIMENT

Figure 1:
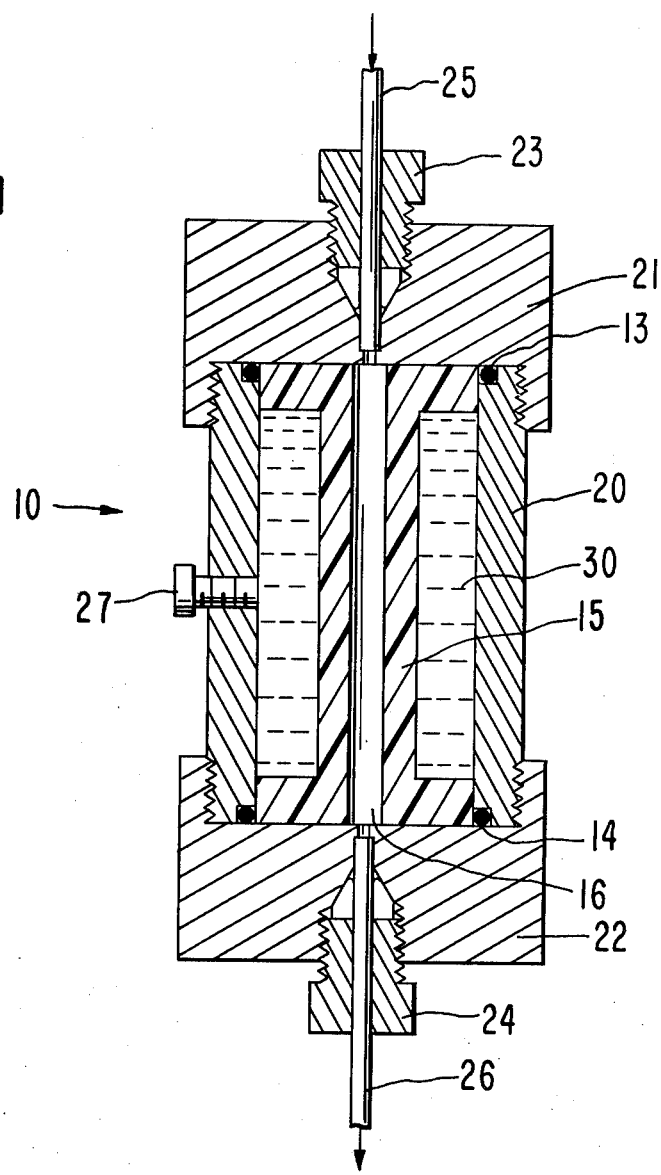
FIG. 1 is a cross-sectional view of a pulse damper according to this invention.

In FIG. 1, a cross-sectional view of a pulse damper 10 according to this invention is shown. The pulse damper 10 is designed for use in a liquid pumping system, such as a liquid chromatography system in which the outflow from a reciprocating pump is delivered in pulses to a flow line leading to a chromatographic column. A plastic spool 15, which is made of a material that is chemically inert with respect to fluids typically used in liquid chromatography, is provided witch an axial bore 16.

The diameter and length of the bore 16 are selected so that the interior volume of the bore 16 is approximately equal to the volume of liquid delivered during each reciprocation stroke of the system's pump. This arrangement has been found to provide a satisfactory compromise between the requirement on the one hand that the volume in the bore 16 be small in order that a small-volume connecting line to the chromatographic column can be used, and the desirability on the other hand that the volume in the bore 16 be large in order to minimize the effect of pulsations attributable to the pumping cycle. For most liquid chromatography applications, the spool 15 may be made of polytetrafluoroethylene, which is a material available under the trademark Teflon.

The spool 15 is encased within a cylindrical housing structure 20 that may advantageously be made of stainless steel. The ends of the spool 15 fit tightly against the inside wall of the housing structure 20, but the greater portion of the surface of the spool is separated from the inside wall of the housing structure 20 so as to form a liquid-tight annular cavity 30 around the bore 16. The ends of the housing structure 20 are covered with threaded end caps 21 and 22, respectively, which are likewise advantageously made of stainless steel. Fittings 23 and 24 are attached to the end caps 21 and 22, respectively, to provide means for connecting inlet and outlet lines 25 and 26 to the end caps 21 and 22, respectively. In this way, unobstructed communication between the inlet line 25 and the outlet line 26 is provided via the axial bore 16. Suitable sealing means, such as the O-rings 13 and 14, are provided to isolate the liquid flowing through the axial bore 16 from the surrounding cavity 30. A sealable fill port 27 is provided in the housing structure 20 whereby the cavity 30 can be filled with a compressible liquid, which for many chromatographic applications may be water.

In operation, when pressure pulses occur in the flow line liquid, the relatively thin flexible walls of the bore 16 are caused to expand radially outward. The liquid filling the cavity 30 thereby compresses in response to the pulsations occuring in the bore 16. Thus, the liquid in the cavity 30 acts as an energy storing means during that portion of the pumping cycle when the pressure in the flow line is rising. During that portion of the pumping cycle when the pressure in the flow line is falling, the energy stored in the liquid in the cavity 30 is transmitted through the walls of the bore 16 back into the flow line liquid, thereby smoothing out the pulsations generated by the pumping mechanism.

The pulse damping technique of this invention is superior to prior art techniques, especially at high pressures (i.e., above 1000 psi), because the damping mechanism utilizes the compressibility of a liquid rather than the compressibility of a plastic body. In considering the damping characteristics of a material, whether solid or liquid, it is important to distinguish between average compressibility and instantaneous compressibility. The average compressibility of a material, whether liquid or solid, is defined by the equation $$x_a = -1/V_1(V_1-V_2/P_1-P_2) \tag{1}$$

where $V_1$ is the volume of the material at atmospheric pressure $P_1$, and $V_2$ is the volume of that same material at the pressure $P_2$. The instantaneous compressibility of a material is defined by the equation $$x_i = -(1/V) \cdot (dV/dP) \tag{2}$$

where V is the volume of the material at pressure P, and $dV/dP$ is the rate of change of the volume V with respect to the pressure P.

Figure 2:
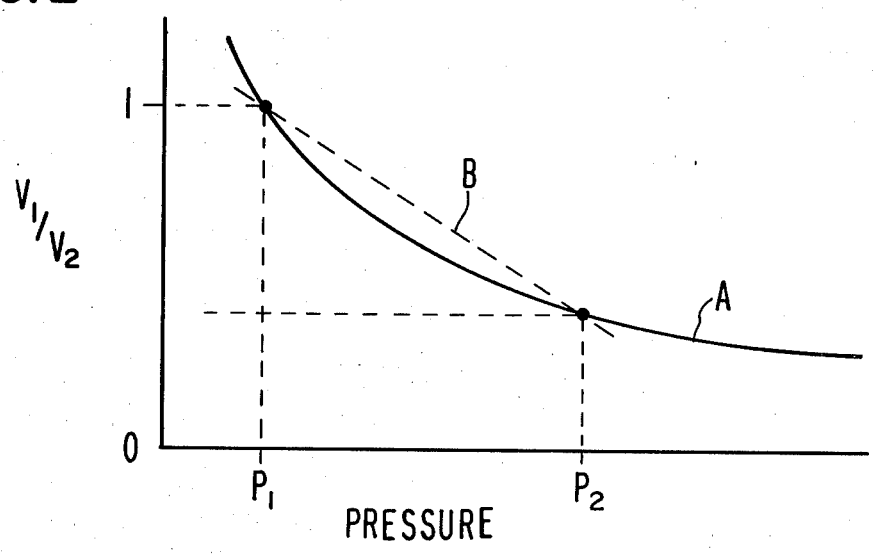
FIG. 2 illustrates graphically the typical variation of relative volume with respect to pressure for a compressible solid or liquid.

In FIG. 2, a typical variation of relative volume $V_1/V_2$ with respect to pressure P for a compressible material, whether solid or liquid, is shown by the solid curve A. The compressibility X of the material at any given value of P is thus proportional to the slope of the curve A at that point P on the abscissa. Because of the changing slope of the curve A, the average comressibility $X_a$ for the material of interest between the pressures $P_1$ and $P_2$ is much larger than the instantaneous compressibility $X_i$ at the pressure $P_2$.

If, on the other hand, the variation of volume with respect to pressure could be represented by a straight line, such as the broken line B in FIG. 2, the average compressibility $X_a$ and the instantaneous compressibility $X_i$ would be identical at any given pressure.

For water, there is only a slight difference between the average compressibility and the instantaneous compressibility for pressures encountered in high-pressure liquid chromatography. Thus, at 5,000 psi, which is a typical pressure for high-pressure liquid chromatographic applications, the average compressibility of water is given by the expression $X_a = 2.98 \times 10^{-6} \text{psi}^{-1}$, and the instantaneous compressibility is given by the expression $X_i = 2.82 \times 10^{-6} \text{psi}^{-1}$.

For polytetrafluoroethylene, however, the difference between the average compressibility and the instantaneous compressibility at high pressures is quite significant. Thus, at 1,000 psi, the values for the average compressibility and the instantaneous compressibility of polytetrafluoroethylene have been experimentally found to be in the vicinity of $X_a = 6.8 \times 10^{-6} \text{psi}^{-1}$ and $X_i = 4.8 \times 10^{-6} \text{psi}^{-1}$, respectively. At 5,000 psi, the values for the average and instantaneous compressibity of polytetrafluoroethylene have been found experimentally to be in the vicinity of $X_a = 4.2 \times 10^{-6} \text{psi}^{-1}$ and $X_i = 2.0 \times 10^{-6} \text{psi}^{-1}$, respectively. Thus, for polytetrafluoroethylene, the average compressibility and the instantaneous compressibility differ greatly at high pressures.

When considering the pulse damping characteristics of a particular material for use in a liquid pumping system, it is necessary to consider the range of pressures $(P_1 - P_2)$ over which the pulse damper must operate. In liquid chromatographic systems, the reciprocating pump generally operates within a very narrow range of pressures. Consequently, for a pulse damper in a liquid chromatography system, the pressure range $(P_1 - P_2)$ is generally small enough so that the instantaneous compressibility $X_i$ of the pulse damping material at the midpoint of the pump's operating pressure range may be considered as equal to the average compressibility $X_a$ of the material in that pressure range to a first approximation. Where the instantaneous compressibility of $X_i$ the pulse damping material at the mid-point of the pump's operating pressure range differs substantially from the average compressibility of that same material over that same operating pressure range, it may be concluded that the compressible material exhibits non-uniform damping characteristics over the operating pressure range of the pump.

In high-pressure pumping applications using a reciprocating pump, a pulse damping mechanism that relies on the compressibility of polytetrafluoroethylene cannot damp pulses uniformly over the entire pressure range of the pump. Such non-uniformity in the pulse damping characteristics of polytetrafluoroethylene results in an inefficient damping performance by a pulse damping device made from that material.

The pulse damping mechanism of the present invention, on the other hand, relies upon the compressibility of a liquid rather than upon the compressibility of a plastic material such as polytetrafluoroethylene. The liquid can be chosen for its uniform pulse damping capability over the pressure range of the pump, irrespective of the chemical properties of the liquid flowing through the flow line, because the liquid used for its pulse damping capability is isolated from the liquid in the flow line.

This invention has been described above in terms of a particular embodiment. Clearly, other embodiments using design parameters appropriate to particular kinds of liquid pumping applications will be readily apparent to those skilled in the art. Thus, the above disclosure is to be construed as illustrative rather than as limiting; and the scope of the invention is defined by the following claims.

What is claimed is:

1. A pulse damper for damping flow pulsations in a fluid passing through a flow line in a high pressure liquid chromatography system, said pulse damper comprising, an elongate member having an axial bore therethrough;

means for coupling said elongate member to said flow line to provide a flow path for said fluid through said pulse damper via said bore, said elongate member being made of a homogeneous non-porous material and having a wall portion that is unsupported by any solid supporting member in a radial direction perpendicular to said axis of said bore, said elongate member being radially expandable at said wall portion when pulses occur in said flow line;

means forming a cavity for retaining a confined liquid around said elongate member, whereby radial expansion of said elongate member causes compression of said liquid in said cavity, said cavity being the space formed between the outer surfaces of said elongate member and the inner surfaces of said means for forming a cavity, wherein said elongate member is made of a material selected from the group consisting of polytetrafluoroethylene and polychlorotrifluoroethylene and wherein said cavity, in operation, is filled with a compressible liquid, said liquid having an average compressibility, Xa, and instantaneous compressibility, Xi, at pressure above 1000 psi such that 100(Xa−Xi)/Xa is substantially less than 50 percent.

2. The pulse damper of claim 1 wherein said elongate member is configured as a spool and wherein said high pressure liquid chromatography system includes a reciprocating pump for delivering fluid to a flow line in pulses.

* * * * *